US006739197B2

(12) United States Patent
Collins et al.

(10) Patent No.: US 6,739,197 B2
(45) Date of Patent: May 25, 2004

(54) ULTRASONIC DIAGNOSTIC IMAGING SYSTEM WITH ELEVATED AND TILTED SCANHEAD CONNECTORS

(75) Inventors: Jack Collins, Woodinville, WA (US); Yas Matsui, Redmond, WA (US); Robert Lincoln, Sammamish, WA (US); Lyle Whelchel, Snohomish, WA (US); Robert Mesaros, Bothell, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 55 days.

(21) Appl. No.: 10/155,505

(22) Filed: May 23, 2002

(65) Prior Publication Data

US 2003/0217600 A1 Nov. 27, 2003

(51) Int. Cl.$^7$ ............................ G01N 29/24; A61B 8/00
(52) U.S. Cl. ............................ 73/628; 73/641; 600/459
(58) Field of Search ............ 73/644, 631; 128/660.01, 128/662.03, 661.01; 600/121, 122, 24, 25

(56) References Cited

U.S. PATENT DOCUMENTS

| | | | | |
|---|---|---|---|---|
| 5,050,610 A | * | 9/1991 | Oaks et al. | 600/437 |
| 5,205,175 A | | 4/1993 | Garza et al. | |
| 5,251,631 A | | 10/1993 | Tsuchiko et al. | |
| 5,255,682 A | * | 10/1993 | Pawluskiewicz et al. | 600/459 |
| 5,615,678 A | * | 4/1997 | Kirkham et al. | 600/459 |
| 5,674,218 A | * | 10/1997 | Rubinsky et al. | 606/20 |
| 5,770,801 A | * | 6/1998 | Wang et al. | 73/644 |
| 5,795,299 A | * | 8/1998 | Eaton et al. | 600/459 |
| 5,882,310 A | | 3/1999 | Marian, Jr. | |

* cited by examiner

*Primary Examiner*—Helen C. Kwok
(74) *Attorney, Agent, or Firm*—W. Brinton Yorks, Jr.

(57) ABSTRACT

An ultrasonic diagnostic imaging system is provided in which the scanhead connectors are elevated and tilted upward. This is provided by a tilted card cage with a backplane mount for the scanhead connectors which extends above the top of the card cage. The elevated and tilted scanhead connectors provide a comfortable position and orientation for the system operator when inserting and removing probe connectors, and the elevated position keeps the probe cables well above the floor and entanglement with the wheels.

14 Claims, 4 Drawing Sheets

ULTRASONIC DIAGNOSTIC IMAGING SYSTEM WITH ELEVATED AND TILTED SCANHEAD CONNECTORS

This invention relates to ultrasonic diagnostic imaging systems and, in particular, to ultrasonic diagnostic imaging systems with scanhead connectors that are easy to access.

Ultrasound systems are designed to work with a variety of probes or scanheads that are designed for specific diagnostic conditions. This is made possible by two or three scanhead connectors on the system into which the user can plug the scanheads chosen for particular examinations. Conventionally the scanhead connectors are located on the vertical front panel of the system below the control panel. This location arises naturally by the use of a card cage for the printed circuit boards of the system which is accessed from the rear of the ultrasound system and has a backplane into which the circuit boards are plugged. This backplane of the card cage is thus located on the front side of the ultrasound system cart, and the scanhead connectors are conventionally located on the outside of this backplane.

This location is inconvenient for the user for several reasons. First, the user must stoop below the control panel to access the connectors. The scanhead must be plugged in by holding the probe connector perfectly vertical, in line with the connector on the system, which can require further bending by the user. Thirdly, this low connection location often leaves the lengthy probe cables dragging on the floor in front of the system, where they can become tangled in the wheels of the ultrasound system cart. It would be desirable to position the scanhead connectors at a location where they can be more conveniently accessed by the user without undue stretching and bending. It would further be desirable to be able to more easily plug the probes into the connectors. It would also be desirable to keep the probe cables off of the floor and away from the wheels of the ultrasound system cart.

In accordance with the principles of the present invention, an ultrasound system is provided with a card cage backplane located in the rear of the ultrasound system which extends above the card cage so as to provide scanhead connectors which are elevated above the card cage. This elevated location does not require the user to bend to plug probes into the system, and keeps the probe cables well above the floor level. In a preferred embodiment the card cage is tilted at an acute angle from vertical to provide ease of access when connecting a probe. In accordance with a further aspect of the present invention, the card cage includes a front plane on the front of the ultrasound system cart with a printed circuit board connector on the outside surface. Printed circuit boards can be plugged into this connector for testing, obviating the need for extender cards when servicing the ultrasound system.

Figure 1:
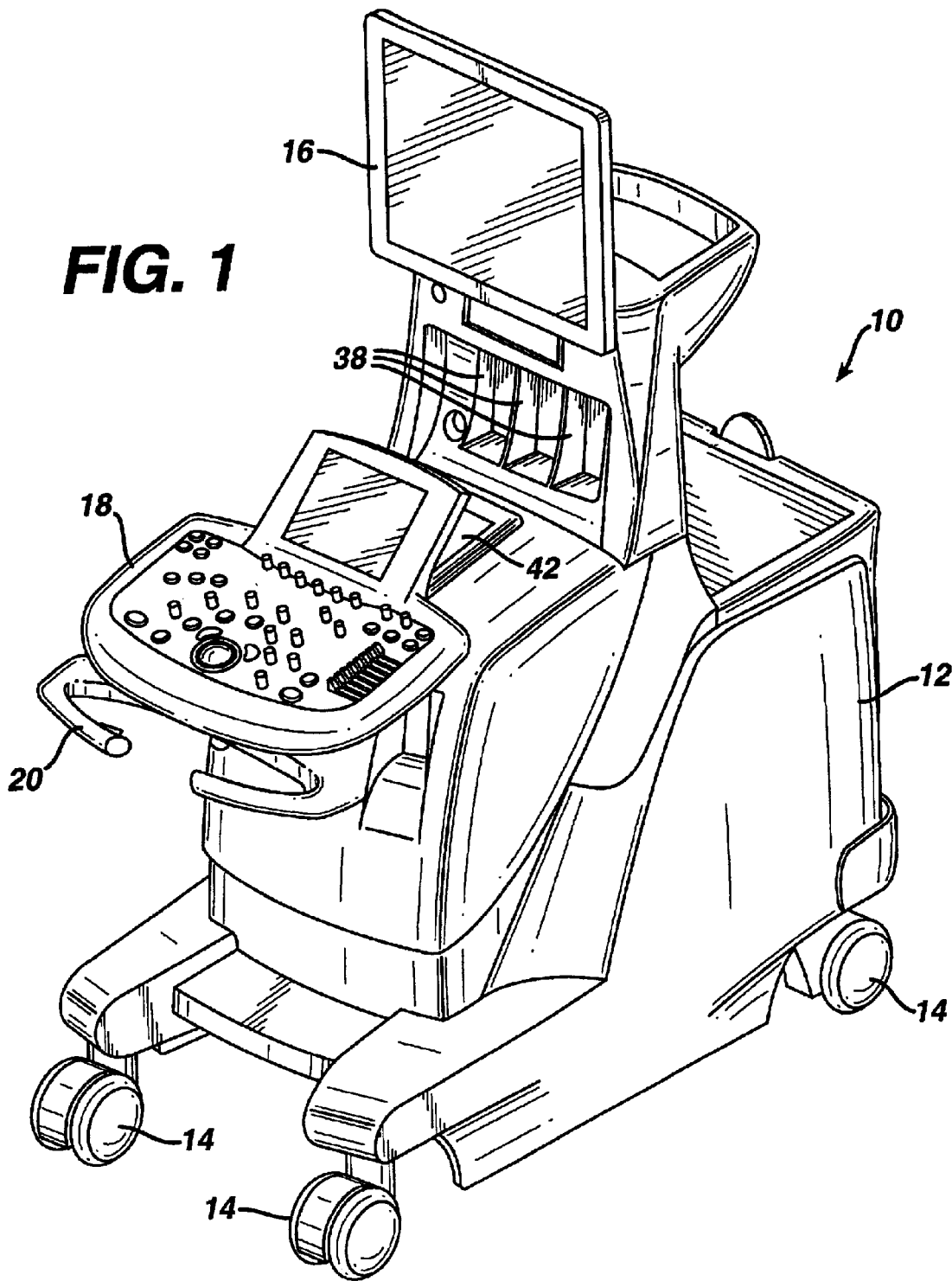
FIG. 1 illustrates a cart-borne ultrasound system in perspective.

Referring first to FIG. 1, a cart-borne ultrasound system 10 is shown in perspective. The cart includes an electronics bay 12 inside of which are located printed circuit boards for electronically processing received ultrasound signals. Located above the electronics bay 12 are three recessed scanhead connectors 38. The ultrasound signals received by the system are processed to produce an image which is displayed on a display 16. The cart is mounted on wheels or casters 14 so that it can be rolled to a lab or a patient's bedside. In the front of the cart is a control panel 18 which contains a number of knobs, buttons, slide switches, and a trackball by which a user operates the ultrasound system. The control panel is mounted above a handle 20 which extends from the front of the ultrasound system. The handle 20 can be used to pull the cart to move it from one location to another. The handle can also be used to raise or lower the control panel by means of a lift mechanism partially visible at 42, which is described more fully in concurrently filed U.S. patent application Ser. No. 10/154,733.

Figure 2:
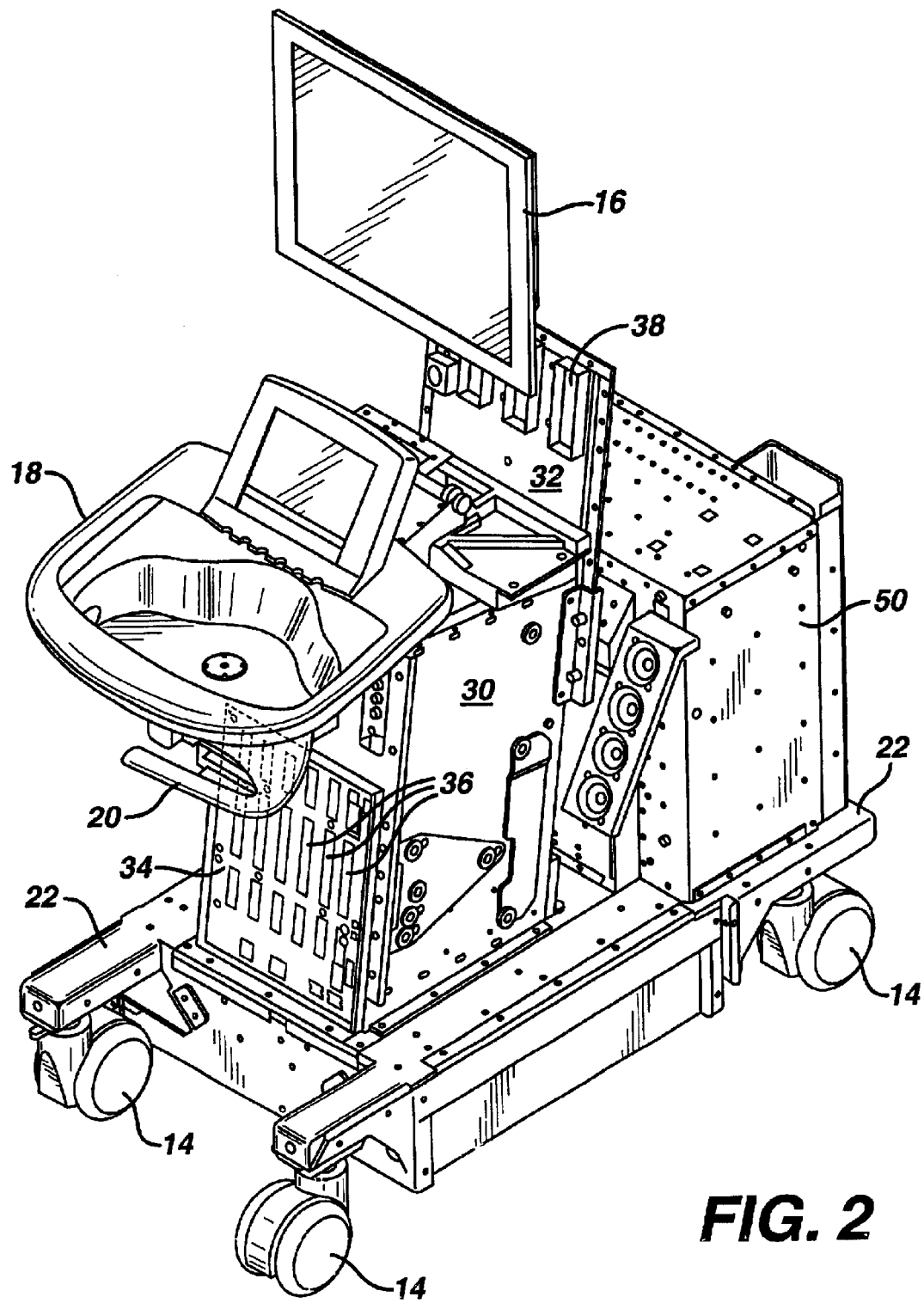
FIG. 2 is a perspective view of the ultrasound system with the outer covers removed.

FIG. 2 illustrates the ultrasound system of FIG. 1 with the covers or "skins" removed. This drawing shows that the ultrasound system is mounted on a frame 22 to which the wheels 14 are connected at the four corners. Mounted on the frame 22 in this embodiment are two card cages 30 and 50. The front card cage 30 contains the acquisition system electronics of the ultrasound system which are contained on printed circuit boards inside the card cage 30. These printed circuit boards plug into connectors on a backplane board 32 which is seen to extend above the top of the card cage 30. Mounted on top of the backplane board 32 are three scanhead connectors 38. When probes are plugged into these scanhead connectors they are connected to ultrasound acquisition circuitry on the printed circuit boards by way of printed circuitry on the backplane board 32. The printed circuit boards in the card cage 30 also connect to connectors on a frontplane board 34 which is below the control panel 18 on the front of the ultrasound system. The frontplane board 34 also has connectors 36 on the outside of the frontplane board. One or more of the printed circuit boards can be removed from the card cage 30 and plugged into the connectors 36 on the outside front of the frontplane board 34. A serviceperson can thus work on the boards when extended in this manner without the need for the usual extender boards generally used in such situations.

Figure 3:
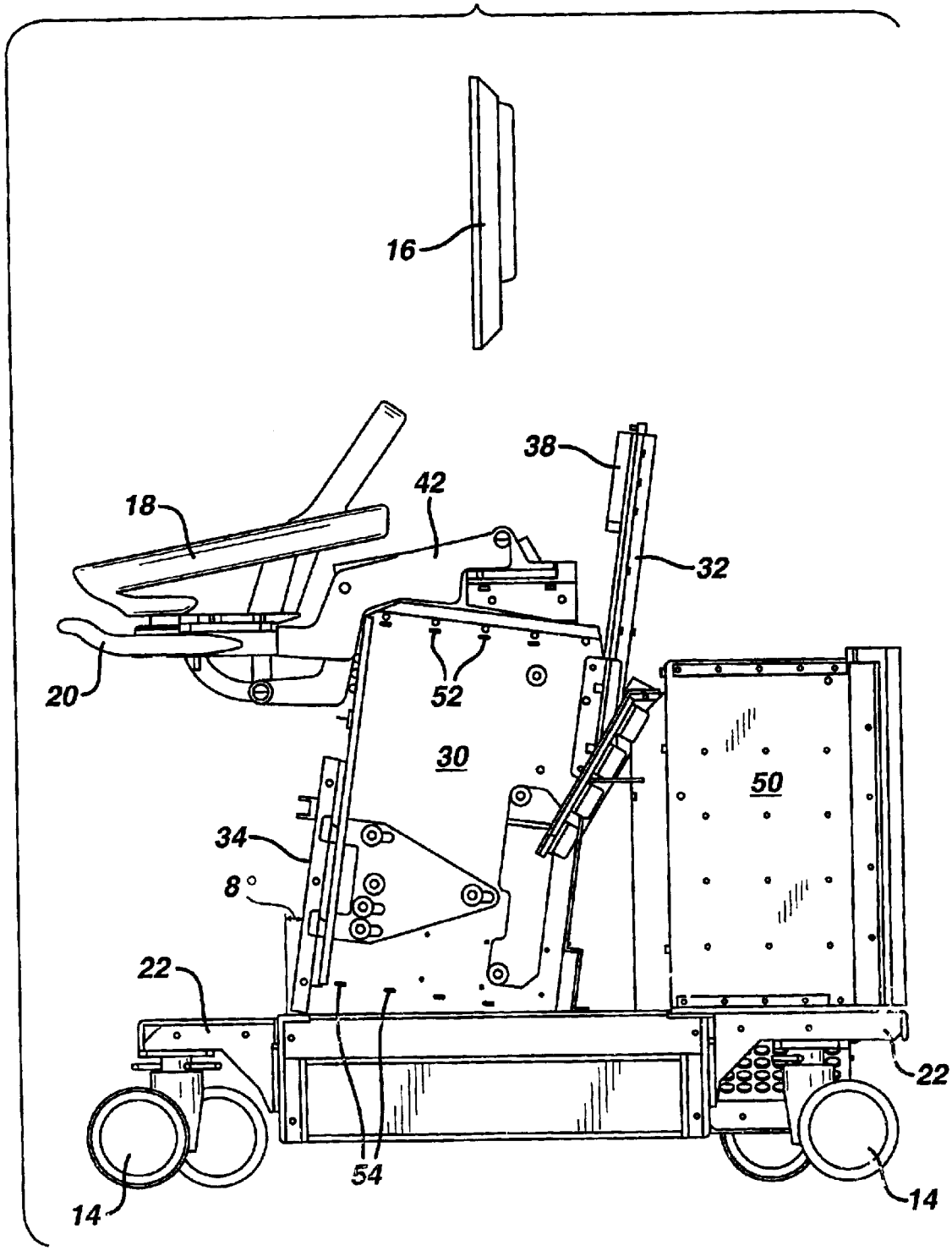
FIG. 3 is a side view of the ultrasound system of FIG. 2 which shows the tilted card cage, elevated scanhead connectors, and front plane.

FIG. 3 is a side view of the ultrasound system of FIG. 2. In this view it is clearly seen that the card cage 30 is not mounted orthogonally to the frame as is customary, but is tilted to the rear. In this embodiment the card cage has a rearward tilt of approximately an 8° acute angle relative to vertical. The printed circuit boards inside the card cage 30 ride in guides mounted at the top and bottom of the card cage as indicated by dashed lines 52 and 54. This rearward tilt causes the scanhead connectors 38 and the printed circuit board connectors 36 on the 30 front of the frontplane 34 to face slightly upward toward a standing ultrasound system user. It has been found to be easier and more convenient for the user to plug probes into the scanhead connectors when given this slight upward orientation, thereby making the ultrasound system more comfortable for users.

Figure 4:
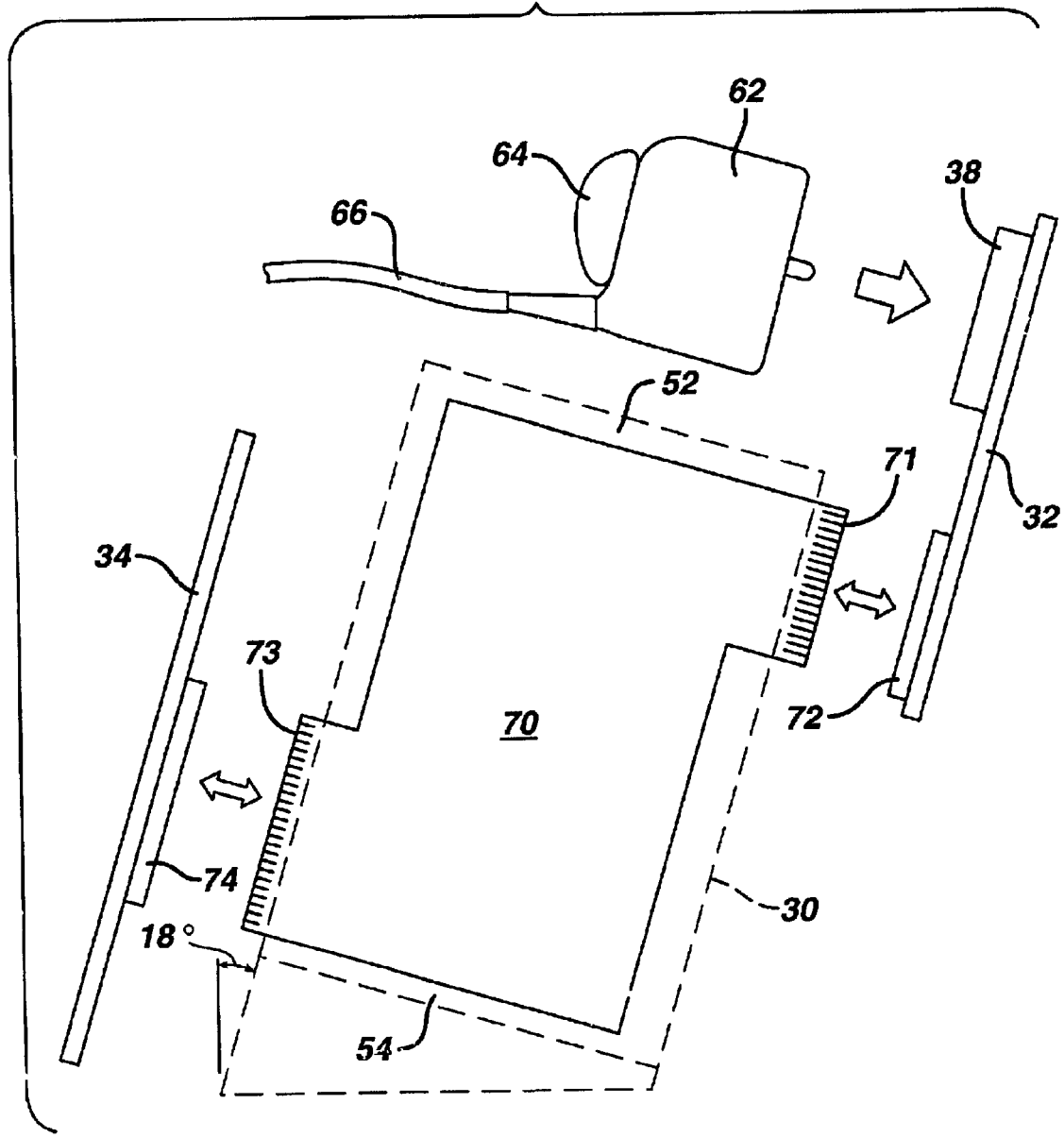
FIG. 4 illustrates the engagement of a printed circuit board with the frontplane and backplane of the card cage.

FIG. 4 illustrates the engagement of printed circuit boards 70 in the tilted card cage 30 with the backplane and frontplane printed circuit board connectors. In this embodiment the card cage is given a tilt of approximately an 18° acute angle to vertical, which causes the scanhead connectors 38 to face upward even more toward a standing system operator. The printed circuit boards 70 have connecting edges 71 and 73 at the front and rear edges of the boards. When a printed circuit board 70 is inserted into the card cage 30 it slides on guides 52 and 54 at the top and bottom of the board until the rear connecting edge 71 engages an edge connector 72 on the backplane 32 at the rear of the card cage 30. When all printed circuit boards are inserted in this manner, the frontplane 34 is mounted on the front of the card cage, with edge connectors 74 engaging the connecting edges 73 on the front of the printed circuit boards 70.

The probe connector 62 engages one of the scanhead connectors 38 as indicated by the arrow at the top of the drawing. When the connector 62 engages the scanhead connector 38 a knob 64 is turned to lock it in place. Signals are thus exchanged between the probe (not shown) at the end of the probe cable and the acquisition circuitry on the printed circuit boards 70 by means of the probe cable 66, the probe connector 62, the scanhead connector 38, the backplane board 32, and the edge connector 72. The probes can easily be plugged into the system scanhead connectors by a standing operator without bending or stooping.

The probe cables can be three to six feet long, or longer. It will be appreciated that if the probe connectors were plugged into connectors at the location of frontplane connectors 36, the conventional location, the cables could easily drag on the floor or become entangled with the wheels 14. But when the probes are plugged into connectors above the card cage 30, there is little danger of dragging the cables on the floor or entangling them with the wheels. The user can scan a patient on an adjacent bed or examination table with the probes, and the probe cables will assume a horizontal or slight catenary position between the elevated connectors on the system and the patient.

In a constructed embodiment of the present invention, it was decided to use card cage 30 for the printed circuit boards of the acquisition portion of the ultrasound system, and to use a rear card cage 50 for the image processing and display electronics of the system. The two card cages will hold all of the electronics of a premium performance ultrasound system. However, it will be appreciated that the electronics of a lower performance ultrasound system could be located in a single card cage, enabling the ultrasound system cart to be shortened by the elimination of the rear card cage 50. With the backplane 32 thus forming the rear of the ultrasound system, a printed circuit board connector 36 can be mounted on the outside of the backplane 32, enabling a printed circuit board to be serviced when plugged into the connector 36 on the back of the ultrasound system without the need for an extender board.

What is claimed is:

1. An ultrasonic diagnostic imaging system including a frame and a card cage mounted on the frame which contains printed circuit boards having electronics which communicate with an ultrasound probe, comprising:

a scanhead connector into which an ultrasound probe may be engaged for communication with at least one of the printed circuit boards, the scanhead connector being approximately vertically oriented above the card cage.

2. The ultrasonic diagnostic imaging system of claim 1, wherein the scanhead connector is oriented at an acute angle relative to vertical.

3. The ultrasonic diagnostic imaging system of claim 1, further comprising a backplane board connected to the card cage and extending above the top of the card cage, wherein the scanhead connector is mounted on the backplane board.

4. The ultrasonic diagnostic imaging system of claim 3, wherein the card cage, the backplane board, and the scanhead connector are tilted at an acute angle relative to vertical.

5. The ultrasonic diagnostic imaging system of claim 4, wherein the acute angle is less than 30°.

6. The ultrasonic diagnostic imaging system of claim 4, wherein the acute angle is less than 20°.

7. The ultrasonic diagnostic imaging system of claim 4, wherein the acute angle is less than 10°.

8. The ultrasonic diagnostic imaging system of claim 3, further comprising a frontplane board mounted on the front of the card cage in engagement with at least one of the printed circuit boards.

9. The ultrasonic diagnostic imaging system of claim 8, further comprising a printed circuit board connector mounted on the outside of at least one of the frontplane board and the backplane board, whereby a printed circuit board can be inserted in the printed circuit board connector for servicing without the need for a printed circuit board extender.

10. A cart-borne ultrasonic diagnostic imaging system including a frame; a plurality of wheels connected to the frame; and a card cage mounted on the frame, comprising:

a backplane board connected to the card cage and extending above the top of the card cage; and a scanhead connector mounted on the backplane board above the top of the card cage, wherein the card cage, the backplane board, and the scanhead connector are tilted at an acute angle relative to vertical.

11. The cart-borne ultrasonic diagnostic imaging system of claim 10, further comprising a plurality of scanhead connectors mounted on the backplane board.

12. The cart-borne ultrasonic diagnostic imaging system of claim 11, wherein the scanhead connectors face upward above the horizontal.

13. The cart-borne ultrasonic diagnostic imaging system of claim 12, wherein the acute angle is less than 20° relative to vertical.

14. The cart-borne ultrasonic diagnostic imaging system of claim 12, wherein the acute angle is less than 10° relative to vertical.

* * * * *